United States Patent [19]

Tinney et al.

[11] 4,022,759

[45] May 10, 1977

[54] TRIPEPTIDES AND METHODS FOR THEIR PRODUCTION

[75] Inventors: Francis John Tinney; Alfred Campbell, both of Ann Arbor, Mich.

[73] Assignee: Parke, Davis & Company, Detroit, Mich.

[22] Filed: Jan. 19, 1976

[21] Appl. No.: 650,095

[52] U.S. Cl. .............. 260/112.5 LH; 260/112.5 R; 424/177
[51] Int. Cl.$^2$ ................................ C07C 103/52
[58] Field of Search ........... 260/112.5 R, 112.5 LH

[56] References Cited

UNITED STATES PATENTS 3,725,380   4/1973   Konig et al. ................ 260/112.5 R

OTHER PUBLICATIONS

J. M. Stewart and J. D. Young, "Solid Phase Peptide Synthesis," Freeman and Co., San Francisco, 1969, pp. 9–13.
J. D. Roberts and M. C. Caserio, "Basic Principles of Organic Chemistry," Benjamin, Inc., New York, 1965, p. 564.
E. Schroder and K. Lubke, "The Peptides," vol. 1, Academic Press, New York, 1965, pp. 108–111.

*Primary Examiner*—Delbert R. Phillips
*Attorney, Agent, or Firm*—Stephen Raines; George M. Richards; David B. Ehrlinger

[57] ABSTRACT

New tripeptides having the formula A-$R_1$-Tyr(benzyl)-Ser(benzyl)-$R_2$ wherein A is t-butoxycarbonyl or cyclohexylcarbonyl, $R_1$ is Trp, His(benzyl), Cys(benzyl) or Pro and $R_2$ is lower alkoxy, hydrazino, amino, lower alkylamino, di(lower alkyl)amino, benzylamino, allylamino, (diethoxyphosphinyl)methylamino, 2-(diethoxyphosphinyl)ethylamino or 2-[[(phenylmethyl)amino]sulfonyl]ethylamino, methods for their production, and the use of said tripeptides as luteinizing hormone releasing factor antagonists.

4 Claims, No Drawings

TRIPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new N-protected tripeptides that are represented by the formula $$A\text{-}R_1\text{-}Tyr(benzyl)\text{-}Ser(benzyl)\text{-}R_2 \quad\quad I$$

wherein A is t-butoxycarbonyl or cyclohexylcarbonyl, $R_1$ is Trp, His(benzyl), Cys(benzyl) or Pro and $R_2$ is lower alkoxy, hydrazino, amino, lower alkylamino, di(lower alkyl)amino, benzylamino, allylamino, (diethoxyphosphinyl)methylamino, 2-(diethoxyphosphinyl)ethylamino or 2-[[(phenylmethyl)amino]sulfonyl]ethylamino.

In formula I, the conventional symbols for amino acid residues of peptide compounds linked thereto are used and each is intended to have the following meaning: Trp, L-tryptophyl; His(benzyl), $N^{im}$-benzyl-L-histidyl; Cys(benzyl), S-benzyl-L-cysteinyl; Pro, L-prolyl; Tyr(benzyl), O-benzyl-L-tyrosyl and Ser(benzyl), O-benzyl-L-seryl or O-benzyl-D-seryl. In addition, the term "lower alkyl" is intended to mean a straight, branched or cyclic saturated hydrocarbon moiety of up to six carbon atoms, such as methyl, ethyl, isopropyl and cyclopropyl and "lower alkoxy" is intended to mean an alkoxy group having a straight, branched or cyclic saturated hydrocarbon moiety of up to six carbon atoms, such as methoxy, ethoxy and isopropoxy. These symbols and terms will also be used in the formulae that follow for other compounds and each such symbol or term should be understood to have the meaning given above.

In accordance with this invention, compounds of the formula I, wherein A and $R_1$ are as previously defined and $R_2$ is lower alkoxy, are produced by removing a protected tripeptide from a resin complex of the following structure $$A\text{-}R_1\text{-}Tyr(benzyl)\text{-}Ser(benzyl)\text{-}resin \quad\quad II$$

wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference, preferably the resin is a cross-linked copolymer comprising 98 to 99 percent polystyrene cross-linked with 1 to 2 percent divinylbenzene, which is attached to the protected tripeptide through a methyleneoxy bridge wherein the methylene group is attached to the polymeric portion of the resin and the oxygen atom is attached to the protected tripeptide and A and $R_1$ are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 to 4 days, preferably 16 to 24 hours, at about 15° to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein $R_2$ is hydrazino, amino, lower alkylamino, di(lower alkyl)amino, benzylamino or allylamino may be prepared by reacting compounds of the formula II wherein A and $R_1$ are as previously defined, with hydrazine, ammonia, lower alkylamine, di(lower alkyl)amine, benzylamine or allylamine.

The resin complex is suspended in a solvent, such as methanol, ethanol, dimethylformamide, etc., at a temperature of from about 0° to 50° C. for periods of from 12 hours to 10 days. When employing less reactive amines, the preferred solvent is dimethylformamide.

The complex resins of the formula II are prepared by coupling a protected amino acid of the formula $$A\text{-}R_1\text{-}OH \quad\quad III$$

wherein A and $R_1$ are as previously defined, with a complex resin of the formula $$Tyr(benzyl)\text{-}Ser(benzyl)\text{-}resin \quad\quad IV$$

in an organic solvent, such as dichloromethane with the aid of dicyclohexylcarbodiimide. The three components may generally be used in about equimolar quantities but excess amounts of the protected amino acid and dicyclohexylcarbodiimide are sometimes advantageous. The reaction is generally conducted at about room temperature for a period of from about 15 minutes to about 16 hours.

The complex resins of the formula IV are prepared by treating complex resins of the formula $$t\text{-butoxycarbonyl-Tyr(benzyl)-Ser(benzyl)-resin} \quad\quad V$$

with a large excess of trifluoroacetic acid utilizing dichloromethane as the solvent at temperatures of from 20° to 30° C. for about 10 minutes.

The complex resins of the formula V are prepared by coupling $$t\text{-butoxycarbonyl-Tyr(benzyl)-OH}$$

to a complex resin of the formula $$Ser(benzyl)\text{-}resin \quad\quad VI$$

using the reaction procedure described for the preparation of compounds of the formula II.

The complex resins of the formula VI are prepared by treating the known complex resins of the formula $$t\text{-butoxycarbonyl-Ser(benzyl)-resin}$$

with trifluoroacetic acid using the reaction procedure for the preparation of compounds of the formula IV.

In accordance with this invention, compounds of the formula I, wherein A and $R_1$ are as previously described and $R_2$ is hydrazino, amino, lower alkylamino, di(lower alkyl)amino, benzylamino, allylamino, are prepared by reacting a compound of the formula I wherein $R_2$ is alkoxy, preferably methoxy with hydrazine, ammonia, lower alkylamine, di(lower alkylamine), benzylamine or allylamine.

The reactions are conducted at temperatures of from about 5° to 100° C. for from 3 hours to four days, preferably about room temperature. Generally, a large excess of hydrazine, preferably used in the form of its hydrate, or amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein A and $R_1$ are as previously defined and $R_2$ is amino, lower alkylamino, di(lower alkyl)amino, benzylamino, allylamino, (diethoxyphosphinyl)methylamino, 2-(diethoxyphosphinyl)ethylamino or 2-[[(phenylmethyl)amino]sulfonyl]ethylamino, are prepared by reacting a compound of the formula

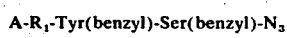
A-R$_1$-Tyr(benzyl)-Ser(benzyl)-N$_3$     VII with ammonia, lower alkylamine, di(lower alkyl)amine, benzylamine, allylamine, (diethoxyphosphinyl)methylamine, 2-(diethoxyphosphinyl)ethylamine or 2-[[(phenylmethyl)amino]sulfonyl]ethylamine in a non-reactive solvent such as dimethylformamide, dioxane, tetrahydrofuran or mixtures thereof. The reaction is carried out at about −30° to about 0° C. for about 12 to 24 hours, preferably −20° C. to 0° C. for from 16 to 19 hours. The two reactants are used in approximately equimolar amounts although a slight excess of amine, about 10 percent, is preferred. When A is t-butoxycarbonyl, care should be taken to avoid the presence of an excess of acid.

The azide compounds of the formula VII are normally prepared in situ by reacting a peptide hydrazide compound of the formula I wherein A and $R_1$ are as previously defined and $R_2$ is hydrazino, with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature between −30° and 0° C. Following the in situ formation of the azide of formula VII and prior to the further reaction of the peptide azide with the appropriate amine to form certain tripeptides of formula I, a tertiary amine such as triethylamine is added to the reaction mixture to neutralize the acid used.

Compounds of the formula I wherein A and $R_1$ are as previously described and $R_2$ is hydrazino, amino, lower alkylamino, di(lower alkyl)amino, benzylamino, allylamino (diethoxyphosphinyl)methylamino, 2-diethoxyphosphinyl)ethylamino or 2-[[(phenylmethyl)amino]sulfonyl]ethylamino are prepared by coupling a compound of the formula

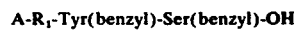
A-R$_1$-Tyr(benzyl)-Ser(benzyl)-OH     VIII with hydrazine, ammonia, lower alkylamine, di(lower alkyl)amine, benzylamine, allylamine, (diethoxyphosphinyl)methylamine, 2-(diethoxyphosphinyl)ethylamine or 2-[[(phenylmethyl)amino]sulfonyl]ethylamine in an inert solvent in the presence of dicyclohexylcarbodiimide.

The above reaction is carried out using approximately equivalent amounts of reactants and dicyclohexylcarbodiimide in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° to 50° C., preferably room temperature for periods of from 10 hours to 5 days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula VIII are prepared by the hydrolysis of a compound of formula I wherein A and $R_1$ are as previously defined and $R_2$ is lower alkoxy. The reaction is conducted at temperatures of from 20° to 30° C. using about 0.25 ml. of a two normal aqueous sodium hydroxide solution and 10 ml. of solvent for each millimole of ester. The compound of formula VIII is isolated after acidification with aqueous citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Tripeptides of this invention were screened for LRF antagonist activity in vitro using rat anterior pituitary cell cultures as described by Vale et al. [Endocrinology, 91, 562 (1972)]. The inhibition of LRF (luteinizing hormone release factor) induced luteinizing hormone (LH) release into the culture medium is the endpoint in this in vitro bioassay.

Following are the results of the above tests on certain preferred compounds.

| | ACTIVITY ABLE FOR IN VITRO TEST IN RAT ANTERIOR PITUITARY CELL CULTURES | | |
|---|---|---|---|
| | Molar Conc. | LH Value ng/ml. | % LH Release Inhibition |
| N$^\alpha$-t-butoxycarbonyl-S-benzyl-L-cysteinyl-O-benzyl-L-tyrosyl-O-benzyl-L-serine N-ethylamide | 5 × 10$^{-7}$ | 20.06 | 76 |
| | 1 × 10$^{-7}$ | 36.04 | 42 |
| | 5 × 10$^{-8}$ | 42.65 | 28 |
| | 1 × 10$^{-8}$ | 45.64 | 22 |
| | LRF Control (5 × 10$^{-10}$) | 56.00 | |
| | Saline Control | 8.90 | |
| | 1 × 10$^{-8}$ | 13.20 | 84 |
| | LRF Control (1 × 10$^{-9}$) | 33.10 | |
| | Saline Control | 9.33 | |
| N$^\alpha$-cyclohexylcarbonyl-N$^{im}$-benzyl-L-histidyl-O-benzyl-L-tyrosyl-O- | 5 × 10$^{-7}$ | 24.69 | 66 |
| | 1 × 10$^{-7}$ | 42.57 | 29 |
| | 5 × 10$^{-8}$ | 44.32 | 25 |

-continued

ACTIVITY TABLE FOR IN VITRO TEST IN RAT ANTERIOR PITUITARY CELL CULTURES

| | Molar Conc. | LH Value ng/ml. | % LH Release Inhibition |
|---|---|---|---|
| benzyl-L-serine N-ethylamide | $1 \times 10^{-8}$ | 43.81 | 26 |
| | LRF Control ($5 \times 10^{-10}$) | 56.00 | |
| | Saline Control | 8.90 | |
| | $1 \times 10^{-6}$ | 22.45 | 74 |
| | LRF Control ($1 \times 10^{-9}$) | 65.08 | |
| | Saline Control | 7.12 | |
| $N^\alpha$-t-butoxycarbonyl-$N^{im}$-benzyl-L-histidyl-O-benzyl-L-tyrosyl-O-benzyl-L-serine N-ethylamide | $5 \times 10^{-7}$ | 28.75 | 58 |
| | $1 \times 10^{-7}$ | 46.45 | 20 |
| | LRF Control ($5 \times 10^{-10}$) | 56.00 | |
| | Saline Control | 8.90 | |
| | $1 \times 10^{-6}$ | 19.29 | 79 |
| | LRF Control ($1 \times 10^{-9}$) | 65.08 | |
| | Saline Control | 7.12 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see *Science*, Vol. 174, No. 4008, October 29, 1971, pages 511–512. Thus, the tripeptides of this invention are useful in controlling ovulation and in restricting fertility.

The invention is illustrated by the following examples.

EXAMPLE 1:

$N^\alpha$-t-Butoxycarbonyl-$N^{im}$-benzyl-L-histidyl-O-benzyl-L-tyrosyl-O-benzyl-L-serine methyl ester A mixture of 50 g. of chloromethylated polystyrene resin having 1.16 mmole of chlorine per gram, and 18.8 g. of $N^\alpha$-t-butoxycarbonyl-O-benzyl-L-serine in 1 liter of ethanol is treated with 6.7 g. of triethylamine and refluxed for 3 days. The resin is separated by filtration, washed with ethanol, water, methanol, dichloromethane and ether, successively, and then dried overnight at 40° C. giving the t-butoxycarbonyl-O-benzyl-L-serine resin.

A tubular flask of 400 ml. capacity, having a sintered glass disc and stopcock at one end and a suitably placed opening for addition of materials at the other is clamped to a motor which imparts a rocking motion to the flask. The flask is charged with (15 g.) of $N^\alpha$-t-butoxycarbonyl-O-benzyl-L-serine resin and 200 ml. of dichloromethane and agitated for one half hour. The liquid is then drained from the flask by connecting a suction, through a trap, to the stopcock. The resin is retained in the flask by means of the sintered glass disc. The $N^\alpha$-t-butoxycarbonyl protecting group is removed by rocking the resin with 100 ml. of trifluoroacetic acid and 100 ml. of dichloromethane for ten minutes. The liquid is drained from the flask and the trifluoroacetate salt of O-benzyl-L-serine resin is washed five times with 200 ml. of dichloromethane each time. The trifluoroacetate salt of the O-benzyl-L-serine resin is converted to O-benzyl-L-serine resin by the addition of 20 ml. of triethylamine in 200 ml. of cold dichloromethane and rocking the reaction for 10 minutes. The flask is drained and the resin again washed five times with 200 ml. of dichloromethane each time. The O-benzyl-L-tyrosine moiety is coupled to the O-benzyl-L-serine resin by adding 7.8 g. of $N^\alpha$-t-butoxycarbonyl-O-benzyl-L-tyrosine in 200 ml. of dichloromethane, shaking for sixty minutes, adding 4.4 g. of dicyclohexylcarbodiimide in 50 ml. of dichloromethane and rocking the reaction flask for 24 hours. The flask is drained and the resin washed three times with 250 ml. of dichloromethane each time. Trifluoroacetic acid (100 ml.) and dichloromethane (100 ml.) are used as above to remove the t-butoxycarbonyl protecting group and the resin drained and washed as before. Triethylamine, 20 ml. in 200 ml. of cold dichloromethane, is used to liberate the O-benzyl-L-tyrosyl-O-benzyl-L-serine resin, which is treated with 7.2 g. of $N^\alpha$-t-butoxycarbonyl-$N^{im}$-benzyl-L-histidine in 200 ml. of dichloromethane, rocked for thirty minutes and 4.4 g. of dicyclohexylcarbodiimide added in 50 ml. of dichloromethane. The coupling reaction is rocked for 24 hours, the flask drained and the resin washed two times with 200 ml. of dichloromethane each time. The resin is then washed from the flask with methanol-chloroform (1:2), three times with 200 ml with methanol, three times with 200 ml., with ether, three times with 200 ml. and is air dried for 2 hours (21.3 g.)

The dried resin (7 g.) is stirred overnight with 50 ml. of triethylamine and 500 ml. of methanol, filtered and the filtrate evaporated to yield 2 g. of $N^\alpha$-t-butoxycarbonyl-$N^{im}$-benzyl-L-histidyl-O-benzyl-L-tyrosyl-O-benzyl-L-serine methyl ester after chromatography on silica gel using chloroform-methanol-water (60:30:5); m.p. 50°–55° C.

The general procedure and equipment for solid phase peptide synthesis is described by Stewart and Young, "Solid Phase Peptide Synthesis", W. H. Freeman and Company, San Francisco, 1969.

EXAMPLE 2

N$^\alpha$ -t-Butoxycarbonyl-N$^{im}$-benzyl-L-histidyl-O-benzyl-L-tyrosyl-O-benzyl-L-serinamide N$^\alpha$ -t-Butoxycarbonyl-N$^{im}$-benzyl-L-histidyl-O-benzyl-L-tyrosyl-O-benzyl-L-serine methyl ester, 0.3 g. is dissolved in 100 ml. of methanol and the solution saturated with ammonia. The reaction is let stand for 2 days in a closed pressure bottle and worked up by evaporating the solvent and chromatographing the residue on silica gel with chloroform-methanol-water (60:30:5) to give 0.22 g.; m.p. 73°–78° C.

EXAMPLE 3

N$^\alpha$ -t-Butoxycarbonyl-N$^{im}$-benzyl-L-histidyl-O-benzyl-L-tyrosyl-O-benzyl-L-serine N-ethylamide N$^\alpha$ -t-Butoxycarbonyl-N$^{im}$-benzyl-L-histidyl-O-benzyl-L-tyrosyl-O-benzyl-L-serine methyl ester, 0.3 g., is dissolved in anhydrous methanol, 100 ml., and treated with an excess, 10 ml., of ethylamine. The reaction is let stand at room temperature for 5 days and worked up as in Example 2 to yield 0.25 g.; m.p. 65°–70° C.

EXAMPLE 4

N$^\alpha$ -Cyclohexylcarbonyl-N$^{im}$-benzyl-L-histidyl-O-benzyl-L-tyrosyl-O-benzyl-L-serine methyl ester N$^\alpha$ -t-Butoxycarbonyl-N$^{im}$-benzyl-L-histidyl-O-benzyl-L-tyrosyl-O-benzyl-serine resin, 14.3 g., prepared as in Example 1 is interrupted at the completion of the second coupling step, deblocked and neutralized, the resin washed with dichloromethane, five times with 200 ml., and treated with 1.8 g. of cyclohexylcarboxylic acid, 20 ml. of dimethylformamide and 200 ml. of dichloromethane. After 1 hour, 2.9 g. of dicyclohexylcarbodiimide in 20 ml. of dichloromethane is added and the mixture agitated overnight. The resin is drained and washed with 200 ml. of dichloromethane five times. The 12.8 g. of N$^\alpha$ -cyclohexylcarbonyl-N$^{im}$-benzyl-L-histidyl-O-benzyl-L-tyrosyl-O-benzyl-L-serine resin which results is stirred with 500 ml. of methanol and 50 ml. of triethylamine for 2 days. The solvent is evaporated and the residue is chromatographed on silica gel using chloroform-methanol-water (60:30:5) to give 5.7 g. of product as a monohydrate; m.p. 130°–135° C.

EXAMPLE 5

N$^\alpha$ -Cyclohexylcarbonyl-N$^{im}$-benzyl-L-histidyl-O-benzyl-L-tyrosyl-O-benzyl-L-serinamide N$^\alpha$ -Cyclohexylcarbonyl-N$^{im}$-benzyl-L-histidyl-O-benzyl-L-tyrsoyl-O-benzyl-L-serine methyl ester, 0.3 g., is reacted with ammonia as in Example 2 to yield 0.25 g. as a monohydrate; m.p. 122°–127° C.

EXAMPLE 6

N$^\alpha$ -Cyclohexylcarbonyl-N$^{im}$-benzyl-L-histidyl-O-benzyl-L-tyrosyl-O-benzyl-L-serine N-ethylamide N$^\alpha$ -Cyclohexylcarbonyl-N$^{im}$-benzyl-L-histidyl-O-benzyl-L-tyrsoyl-O-benzyl-L-serine methyl ester, 0.3 g., is reacted with ethylamine as in Example 3 to yield 0.26 g. as a hemihydrate; m.p. 115°–120° C.

EXAMPLE 7

N$^\alpha$ -t-Butoxycarbonyl-S-benzyl-L-cysteinyl-O-benzyl-L-tyrsoyl-O-benzyl-L-serinamide N$^\alpha$ -t-Butoxycarbonyl-S-benzyl-L-cysteinyl-O-benzyl-L-tyrsoyl-O-benzyl-L-serine methyl ester, 1.0 g., in 25 ml. of methanol is treated with gaseous ammonia to saturation and let stand, stoppered, at room teperature for 2 to 4 days. The progress of the reaction is followed by thin layer chromatography. The methanol is removed by evaporation under reduced pressure and the crude amide is purified by chromatography on silica gel using 15% methanol in ethyl acetate; $[\alpha]_D^{25}$ –13° (c 1, DMF).

N$^\alpha$ -t-Butoxycarbonyl-S-benzyl-L-cysteinyl-O-benzyl-L-tyrosyl-O-benzyl-L-serine methyl ester is obtained by stirring N$^\alpha$ -t-butoxycarbonyl-S-benzyl-L-cysteinyl-O-benzyl-L-tyrosyl-O-benzyl-L-serine resin in absolute methanol containing 5% of triethylamine for 24 hours at room temperature. The solution is filtered and evaporated. The crude ester is purified by chromatography on silica gel using ethyl acetate containing 0 to 5% methanol; $[\alpha]_D^{23}$ –14° (c 1.0, DMF)

N$^\alpha$ -t-Butoxycarbonyl-S-benzyl-L-cysteinyl-O-benzyl-L-tyrosyl-O-benzyl-L-serine resin is obtained by the solid phase procedure as described in Example 9; using 20 g. of N$^\alpha$ -t-butoxycarbonyl-O-benzyl-L-serine resin containing 0.018 mol of N$^\alpha$ -t-butoxycarbonyl-O-benzyl-L-serine, 26.8 g., 0.072 mol, of N$^\alpha$ -t-butoxycarbonyl-O-benzyl-L-tyrosine and 22.4 g., 0.072 mol, of N$^\alpha$ -t-butoxycarbonyl-S-benzyl-L-cysteine.

EXAMPLE 8

N$^\alpha$ -t-Butoxycarbonyl-S-benzyl-L-cysteinyl-O-benzyl-L-tyrosyl-O-benzyl-L-serine N-ethylamide N$^\alpha$ -t-Butoxycarbonyl-S-benzyl-L-cysteinyl-O-benzyl-L-tyrosyl-O-benzyl-L-serine methyl ester, 0.03 mol, in 20 ml. of 50l % ethylamine in anhydrous methanol is let stand at room temperature for 24 hours. The methanol and ethylamine are removed by evaporation under reduced pressure and the crude product chromatographed on silica gel using 10% methanol in ethyl acetate. The selected eluate fractions, as determined by thin layer chromatography, are evaporated and the residue dissolved in 25 ml. of methanol, filtered through a filter aid (Super Cel - Johns-Manville, Denver Colo.) and the filtrate evaporated under reduced pressure; $[\alpha]_D^{25}$ –8.2° (c 1.0, DMF).

EXAMPLE 9

N$^\alpha$ -t-Butoxycarbonyl-L-prolyl-O-benzyl-L-tyrosyl-O-benzyl-L-serine N-ethylamide N$^\alpha$ -t-Butoxycarbonyl-L-prolyl-O-benzyl-L-tyrosyl-O-benzyl-L-serine methyl ester, 2.1 g., 0.03 mol, is reacted with ethylamine in methanol as in Example 8. The product is obtained as a white glass, 1.2 g.; $[\alpha]_D^{25}$ –23° (c 1.0, methanol).

N$^\alpha$ -t-Butoxycarbonyl-L-prolyl-O-benzyl-L-tyrosyl-O-benzyl-L-serine methyl ester is obtained by solid phase procedure with the following steps:

1. Resin, 20 g., containing 0.9 mmol of N$^\alpha$ -t-butoxycarbonyl-O-benzyl-L-serine per gram (equivalent to 5.33 g., 0.018 mol) is introduced into a shaker in 150 ml. of dichloromethane and agitated for 15 minutes followed by draining off the solvent.

2. Trifluoroacetic acid in dichloromethane (1:1), 150 ml., is introduced and shaking carried on for 30 minutes followed by draining off the liquid.

3. The resin is washed four times with 150 ml. of dichloromethane, using 10 minutes of shaking for each wash.

4. Triethylamine, 10 ml., in 140 ml. of dichloromethane is introduced and the mixture shaken for 15 minutes and then the solution is drained out.

5. The resin is washed three times with 150 ml. of dichloromethane.

6. A solution of 26.8 g., 0.072 mol, of $N^\alpha$-t-butoxycarbonyl-O-benzyl-L-tyrosine in 150 ml. of dichloromethane is added and the mixture shaken for 15 minutes, and the solution is drained out.

7. Dichloromethane, 150 ml., is added followed by a 12.4 ml. of a solution of dicyclohexylcarbodiimide (6.18 g., 0.06 mmol) in dichloromethane and the shaking is continued overnight and the solution finally drained out.

8. The resin is washed three times with 250 ml. of dichloromethane.

9. Steps 2–8 are repeated except that Step 6 uses 15.48 g., 0.072 mol, of $N^\alpha$-t-butoxycarbonyl-L-proline.

10. Following the repeat of Step 8, the resin is washed three times with 150 ml. of absolute methanol and removed from the shaker in the final wash and is collected on a filter.

11. The resin is suspended in 250 ml. of absolute methanol containing 10 ml. of triethylamine and stirred at room temperature overnight. The resin is removed by filtration and rinsed with methanol. Evaporation of the filtrates gives the crude ester as a brown oil. The product is purified by chromatography on silica gel using 5% methanol in ethyl acetate. The appropriate fractions are chosen by thin layer chromatography, evaporated and the product held at high vacuum to remove solvent; 6.2 g.; $[\alpha]_D^{25}$ −25° (c 1.0 methanol).

EXAMPLE 10

$N^\alpha$-Cyclohexylcarbonyl-L-prolyl-O-benzyl-L-tyrosyl-O-benzyl-L-serinamide $N^\alpha$-Cyclohexylcarbonyl-L-prolyl-O-benzyl-L-tyrosyl-O-benzyl-L-serine methyl ester is reacted with ammonia in methanol in the manner of Example 7 $[\alpha]_D^{25}$ −33° (c 1.0, methanol).

$N^\alpha$-Cyclohexylcarbonyl-L-prolyl-O-benzyl-L-tyrosyl-O-benzyl-L-serine methyl ester is obtained by the following procedure:

1. Resin, 20 g., containing 0.9 mmol of $N^\alpha$-t-butoxycarbonyl-O-benzyl-L-serine per gram (equivalent to 5.33 g., 0.018 mol) is introduced into a shaker in 150 ml. of dichloromethane and agitated for fifteen minutes followed by draining off the solvent.

2. Trifluoroacetic acid in dichloromethane (1:1), 150 ml., is introduced and shaking carried on for 30 minutes followed by draining off the liquid.

3. The resin is washed four times with 150 ml. of dichloromethane, using 10 minutes of shaking for each wash.

4. Triethylamine, 10 ml., in 140 ml. of dichloromethane is introduced and the mixture shaken for 15 minutes and then the solution is drained out.

5. The resin is washed three times with 150 ml. of dichloromethane.

6. A solution of 26.8 g., 0.072 mol, of $N^\alpha$-t-butoxycarbonyl-O-benzyl-L-tyrosine in 150 ml. of dichloromethane is added and the mixture shaken for 15 minutes, and the solution is drained out.

7. Dichloromethane, 150 ml., if added followed by a 12.4 ml. of a solution of dicyclohexylcarbodiimide (6.18 g., 0.06 mol) in dichloromethane and the shaking is continued overnight and the solution finally drained out.

8. The resin is washed three times with 150 ml. of dichloromethane.

9. Steps 2–7 are repeated except that Step 6 uses 15.48 g., 0.072 mol, of $N^\alpha$-t-butoxycarbonyl-L-proline.

10. The resin is washed three times with 150 ml. of dichloromethane.

11. Trifluoroacetic acid in dichloromethane (1:1), 150 ml., is introduced and shaking carried on for 30 minutes followed by draining off the liquid.

12. The resin is washed four times with 150 ml. of dichloromethane, using ten minutes of shaking for each wash.

13 Triethylamine, 10 ml., in 140 ml. of dichloromethane is introduced and the mixture shaken for 15 minutes and then the solution is drained out.

14. The resin is washed three times with 150 ml. of dichloromethane.

15. A solution of 8.6 g., 0.072 mol, of cyclohexylcarboxylic acid in 150 ml. of dichloromethane is added and the mixture shaken for 15 minutes, and the solution is drained out.

16. Dichloromethane, 150 ml., is added followed by a 12.4 ml. of a solution of dicyclohexylcarbodiimide (6.18 g., 0.06 mol) in dichloromethane and the shaking is continued overnight and the solution finally drained out.

17. The resin is washed three times with 150 ml. of dichloromethane.

18. The resin is washed three times with 150 ml. of absolute methanol and removed from the shaker in the final wash and is collected on a filter.

19. The resin is suspended in 250 ml. of absolute methanol containing 10 ml. of triethylamine and stirred at room temperature overnight. The resin is removed by filtration and rinsed with methanol. Evaporation of the filtrates gives the crude ester as a brown oil. The product is purified by chromatography on silica gel using 5% methanol in ethyl acetate. The appropriate fractions are chosen by thin layer chromatography, evaporated and the product held at high vacuum to remove solvent, 6.8 g.; $[\alpha]_D^{25}$ −27° (c 1.0, methanol).

EXAMPLE 11

$N^\alpha$-t-Butoxycarbonyl-$N^{im}$-benzyl-L-histidyl-O-benzyl-L-tyrosyl-O-benzyl-L-serinamide The dried tripeptide of resin of Example 1 is added to a cold 10° C. solution of 150 ml. of methanol saturated with gaseous ammonia. The flask is tightly stoppered and the mixture is stirred for 2 days at room temperature. The flask is then cooled, opened, and the mixture filtered. The resin is washed with 50 ml. of hot dimethylformamide and the combined filtrate is evaporated. Ether is added to give the tripeptide amide as a white solid which is purified according to the procedure of Example 2.

EXAMPLE 12

$N^\alpha$-t-Butoxycarbonyl-$N^{im}$-benzyl-L-histidyl-O-benzyl-L-tyrosyl-O-benzyl-L-seryl hydrazide $N^\alpha$-t-Butoxycarbonyl-$N^{im}$-benzyl-L-histidyl-O-benzyl-L-tyrosyl-O-benzyl-L-serine methyl ester, 0.3 g., 0.38 mmol, is dissolved in 100 ml. of methanol and treated with an excess of hydrazine hydrate. The reaction is let stand at room temperature for 2 days and the solvent is then evaporated and the residue chromatographed on silica gel, using chloroform-methanol-water (60:30:5) to yield 0.2 g., m.p. 80°–85° C.

EXAMPLE 13

$N^\alpha$-Cyclohexylcarbonyl-$N^{im}$-benzyl-L-histidyl-O-benzyl-L-tyrosyl-O-benzyl-L-seryl hydrazide $N^\alpha$-Cyclohexylcarbonyl-$N^{im}$-benzyl-L-histidyl-O-benzyl-L-tyrosyl-O-benzyl-serine methyl ester, 0.3 g., 0.37 mmol, is dissolved in 100 ml. of methanol and treated with an excess of hydrazine hydrate. The reaction is let stand at room temperature for 2 days and the solvent is then evaporated and the residue chromatographed on silica gel, using chloroform-methanol-water (60:30:5), to yield 0.18 g. as a hemi-hydrate; m.p. 121°–126° C.

EXAMPLE 14

$N^\alpha$-t-Butoxycarbonyl-L-prolyl-O-benzyl-L-tyrosyl-O-benzyl-L-serinamide $N^\alpha$-t-Butoxycarbonyl-L-prolyl-O-benzyl-L-tyrosyl-O-benzyl-L-serine methyl ester, 0.5 g., is treated with 10 ml. of methanol saturated with gaseous ammonia for 2 days at room temperature. The solvent is removed under reduced pressure and the amide purified by chromatography over silica gel using a mixture of ethyl acetate:methanol 85:15 to yield 0.25 g.; $[\alpha]_D^{23}$ −23.6° (c 1.01, methanol).

EXAMPLE 15

$N^\alpha$-t-Butoxycarbonyl-L-prolyl-O-benzyl-L-tyrosyl-O-benzyl-L-serine hydrazide $N^\alpha$-t-Butoxycarbonyl-L-prolyl-O-benzyl-L-tyrosyl-O-benzyl-L-serine methyl ester, 0.5 g., is dissolved in 10 ml. of methanol containing 0.25 g. of hydrazine hydrate. The mixture is kept at 50° C. for 2 hours and the solvent is removed under reduced pressure. The pure hydrazide is obtained as a granular solid by repeated precipitation from a concentrated solution in ethanol by the addition of ethyl acetate; $[\alpha]_D^{23}$ −26° (c 1.02, methanol).

$N^\alpha$-t-Butoxycarbonyl-L-prolyl-O-benzyl-L-tyrosyl-O-benzyl-L-serine methyl ester is obtained by stirring $N^\alpha$-t-butoxycarbonyl-L-prolyl-O-benzyl-L-tyrosyl-O-benzyl-L-serine resin in absolute methanol containing 10% of triethylamine for 24 hours at room temperature. The solution is filtered and evaporated. The crude ester is purified by chromatography using silica gel and ethyl acetate; $[\alpha]_D^{23}$ −25° (c 1.0, methanol).

$N^\alpha$-t-Butoxycarbonyl-L-prolyl-O-benzyl-L-tyrosyl-O-benzyl-L-serine resin is obtained by the solid phase procedure as described in Example 9 using 10 g. of $N^\alpha$-t-butoxycarbonyl-O-benzyl-L-serine resin (containing 0.018 mol of $N^\alpha$-t-butoxycarbonyl-O-benzyl-L-serine), 11.2 g., 0.036 mol of $N^\alpha$-t-butoxycarbonyl-O-benzyl-L-tyrosine, and 6 g., 0.036 mol of $N^\alpha$-t-butoxycarbonyl-L-proline.

EXAMPLE 16

$N^\alpha$-Cyclohexylcarbonyl-L-prolyl-O-benzyl-L-tyrosyl-O-benzyl-L-serine N-ethylamide $N^\alpha$-Cyclohexylcarbonyl-L-prolyl-O-benzyl-L-tyrosyl-O-benzyl-L-serine methyl ester, 0.5 g., is reacted with a 50% solution of ethylamine in methanol at room temperature for twenty four hours. The solvent is removed under reduced pressure and the residue purified by chromatography over silica gel using ethyl acetate containing 5% methanol. The product is a glass $[\alpha]_D^{23}$ −32° (c1.05, methanol).

EXAMPLE 17

$N^\alpha$-Cyclohexylcarbonyl-L-prolyl-O-benzyl-L-tyrosyl-O-benzyl-L-seryl hydrazide $N^\alpha$-Cyclohexylcarbonyl-L-prolyl-O-benzyl-L-tyrosyl-O-benzyl-L-serine methyl ester, 0.5 g., is reacted with hydrazine as described in Example 12. The purified product is a granular solid $[\alpha]_D^{23}$ −34° (c 1.02, methanol).

EXAMPLE 18

$N^\alpha$-Cyclohexylcarbonyl-S-benzyl-L-cysteinyl-O-benzyl-L-tyrosyl-O-benzyl-L-serine methyl ester $N^\alpha$-Cyclohexylcarbonyl-S-benzyl-L-cysteinyl-O-benzyl-L-tyrosyl-O-benzyl-L-serine methyl ester is obtained by reacting $N^\alpha$-t-butoxycarbonyl-L-serine resin (10 g.) successively with 11.2 g., 30 mmol of $N^\alpha$-t-butoxycarbonyl-O-benzyl-L-tyrosine, 9.4 g., 30 mmol, of $N^\alpha$-t-butoxycarbonyl-S-benzyl-L-cysteine and 3.9 g., 30 mmol, of cyclohexane carboxylic acid in the solid phase procedure according to Example 10. The resin is suspended in 250 ml. of absolute methanol containing 25 ml. of triethylamine at room temperature for 20 hours. The resin is removed by filtration. Evaporation of the filtrate gives the crude ester which is purified by chromatography over silica gel in ethyl acetate. The appropriate fractions are chosen by thin layer chromatography, evaporated, and the product held at high vacuum to remove solvents; 3.4 g., $[\alpha]_D^{23}$ −25° (c 1.01, methanol).

EXAMPLE 19

$N^\alpha$-Cyclohexylcarbonyl-S-benzyl-L-cysteinyl-O-benzyl-L-tyrosinyl-O-benzyl-L-serinamide $N^\alpha$-Cyclohexylcarbonyl-S-benzyl-L-cysteinyl-O-benzyl-L-tyrosyl-O-benzyl-L-serine methyl ester, 0.5 g., is reacted with ammonia and purified as described in Example 2. The product is a glass $[\alpha]_D^{25}$ −24° (c 1.03, methanol).

EXAMPLE 20

$N^\alpha$-Cyclohexylcarbonyl-S-benzyl-L-cysteinyl-O-benzyl-L-tyrosyl-O-benzyl-L-serine N-ethylamide $N^\alpha$-Cyclohexylcarbonyl-S-benzyl-L-cysteinyl-O-benzyl-L-tyrosinyl-O-benzyl-L-serine methyl ester, 0.4 g., is reacted with ethylamine as described in Example 3. The pure amide is a white glass $[\alpha]_D^{23}$ −20° (c 1.05, methanol).

EXAMPLE 21

$N^\alpha$-Cyclohexylcarbonyl-S-benzyl-L-cysteinyl-O-benzyl-L-tyrosyl-O-benzyl-L-seryl hydrazide $N^\alpha$-Cyclohexylcarbonyl-S-benzyl-L-cysteinyl-O-benzyl-L-tyrosyl-O-benzyl-L-serine methyl ester, 0.5 g., is reacted with hydrazine as described in Example 12. The purified product (0.2 g.) is a granular solid; $[\alpha]_D^{23}$ −22° (c 1.03, methanol).

EXAMPLE 22

$N^\alpha$-t-Butoxycarbonyl-S-benzyl-L-cysteinyl-O-benzyl-L-tyrosyl-O-benzyl-L-serine methyl ester $N^\alpha$-t-Butoxycarbonyl-S-benzyl-L-cysteinyl-O-benzyl-L-tyrosyl-O-benzyl-L-serine methyl ester is obtained by reacting $N^\alpha$-t-butoxycarbonyl-L-serine resin (10 g.) successively with 11.2 g., 30 mmol, of $N^\alpha$-t-butoxycarbonyl-O-benzyl-L-tyrosine and 9.4 g., 30 mmol, of $N^\alpha$-t-butoxycarbonyl-S-benzyl-L-cysteine in the solid phase procedure described in Example 10. The crude ester is obtained in the manner described in Example 10 and is purified chromatographically to give a colorless glass $[\alpha]_D^{23} -14°$](c 1.05, methanol).

EXAMPLE 23

$N^\alpha$-t-Butoxycarbonyl-S-benzyl-L-cysteinyl-O-benzyl-L-tyrosyl-O-benzyl-L-seryl hydrazide $N^\alpha$-t-Butoxycarbonyl-S-benzyl-L-cysteinyl-O-benzyl-L-tyrosyl-O-benzyl-L-serine methyl ester, 0.5 g., is reacted with hydrazine hydrate as described in Example 12 to give the hydrazide as a granular solid 0.25 g., $[\alpha]_D^{23} -21°$ (c 1.03, methanol).

EXAMPLE 24

$N^\alpha$-t-Butoxycarbonyl-$N^{im}$-benzyl-L-histidyl-O-benzyl-L-tyrosyl-O-benzyl-D-serine methyl ester $N^\alpha$-t-butoxycarbonyl-O-benzyl-D-serine resin (10 g., 33.9 mmol) is treated successively with 11.2 g., 30 mmol, $N^\alpha$-t-butoxycarbonyl-O-benzyl-L-tyrosine and $N^\alpha$-t-butoxycarbonyl-$N^{im}$-benzyl-L-histidine (10.5 g.) by the solid phase procedure described in Example 9. The ester is obtained and purified; also as described in Example 9 giving a white glass; 4.2 g.; $[\alpha]_D^{25} -5.5°$ (c 1.02, methanol).

$N^\alpha$-t-butoxycarbonyl-O-benzyl-D-serine resin is prepared according to the procedure for preparing the corresponding L form of the resin which is described in a text by Stewart and Young, "Solid Phase Peptide Synthesis", W. H. Freeman & Company, San Francisco, 1969.

EXAMPLE 25

$N^\alpha$-t-Butoxycarbonyl-$N^{im}$-benzyl-L-histidyl-O-benzyl-L-tyrosyl-O-benzyl-D-serinamide $N^\alpha$-t-Butoxycarbonyl-$N^{im}$-benzyl-L-histidyl-O-benzyl-L-tyrosyl-O-benzyl-D-serine methyl ester, 0.5 g., is reacted for three days with ammonia in methanol solution and purified as described in Example 2. The product is a white glass; $[\alpha]_D^{25} + 1.9°$ (c 1.03, methanol).

EXAMPLE 26

$N^\alpha$-t-Butoxycarbonyl-$N^{im}$-benzyl-L-histidyl-O-benzyl-L-tyrosyl-O-benzyl-D-seryl hydrazide $N^\alpha$-t-Butoxycarbonyl-$N^{im}$-benzyl-L-histidyl-O-benzyl-L-tyrosyl-O-benzyl-D-serine methyl ester, 0.3 g., is dissolved in 15 ml. of methanol containing an excess of hydrazine hydrate. The mixture is warmed to 50° C. for 2 hours before reoving the solvent under reduced pressure. The residue is purified by being precipitated three times from a concentrated ethanol solution using cyclohexane to give the pure hydrazide as a white granular powder, 0.15 g.; $[\alpha]_D^{23} + 1.5°$ (c 1.03, methanol).

We claim:

1. A tripeptide represented by the formula

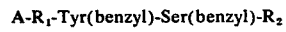

A-$R_1$-Tyr(benzyl)-Ser(benzyl)-$R_2$ wherein A is t-butoxycarbonyl or cyclohexylcarbonyl, $R_1$ is Trp, His(benzyl), Cys(benzyl) or Pro and $R_2$ is lower alkoxy, hydrazino, amino, lower alkylamino, di(lower alkyl)amino, benzylamino, allylamino, (diethoxyphosphinylmethyl)amino, 2-(diethoxyphsophinyl)ethylamino or 2-[[(phenylmethyl)amino]sulfonyl]ethylamino.

2. The compound of claim 1 having the name $N^\alpha$-t-butoxycarbonyl-$N^{im}$-benzyl-L-histidyl-O-benzyl-L-tyrosyl-O-benzyl-L-serine N-ethylamide.

3. The compound of claim 1 having the name $N^\alpha$-cyclohexylcarbonyl-$N^{im}$-benzyl-L-histidyl-O-benzyl-L-tyrosyl-O-benzyl-L-serine N-ethylamide.

4. The compound of claim 1 having the name $N^\alpha$-t-butoxycarbonyl-S-benzyl-L-cysteinyl-O-benzyl-L-tyrosyl-O-benzyl-L-serine N-ethylamide.

* * * * *